United States Patent
Strandburg et al.

(10) Patent No.: US 7,439,276 B2
(45) Date of Patent: Oct. 21, 2008

(54) FROTH AND DURABLE FOAM OF DISPERSED OLEFIN POLYMERS, METHODS OF MAKING FOAM AND ARTICLES PREPARED FROM SAME

(75) Inventors: Gary M. Strandburg, Mount Pleasant, MI (US); Mark W. VanSumeren, Midland, MI (US); Shaofu Wu, Sugar Land, TX (US); Luther E. Stockton, Midland, MI (US); David R. Speth, Midland, MI (US); Brad M. Moncla, Lake Jackson, TX (US); Matthew J. Kalinowski, Freeland, MI (US)

(73) Assignee: Dow Global Technologies Inc., Midland, MI (US)

( * ) Notice: Subject to any disclaimer, the term of this patent is extended or adjusted under 35 U.S.C. 154(b) by 167 days.

(21) Appl. No.: 10/566,612

(22) PCT Filed: Aug. 25, 2004

(86) PCT No.: PCT/US2004/027593

§ 371 (c)(1),
(2), (4) Date: Jan. 31, 2006

(87) PCT Pub. No.: WO2005/021622

PCT Pub. Date: Mar. 10, 2005

(65) Prior Publication Data

US 2006/0211781 A1    Sep. 21, 2006

(51) Int. Cl.
*C08L 47/00*    (2006.01)

(52) U.S. Cl. .......................... 521/140; 521/50; 521/134
(58) Field of Classification Search ............... 428/304; 521/61, 50, 58, 62, 95, 142, 140
See application file for complete search history.

(56) References Cited

U.S. PATENT DOCUMENTS

| | | | |
|---|---|---|---|
| 3,573,152 A | 3/1971 | Wiley et al. | |
| 3,740,353 A | 6/1973 | Patrick et al. | |
| 4,001,158 A | 1/1977 | Lindemann | |
| 4,045,378 A | 8/1977 | Maxwell | |
| 4,540,718 A | 9/1985 | Senda | |
| 4,824,720 A | 4/1989 | Malone | |
| 4,877,814 A | 10/1989 | Ito | |
| 4,931,484 A | 6/1990 | Hovis et al. | |
| 4,990,541 A | 2/1991 | Nielsen et al. | |
| 5,100,924 A | 3/1992 | Senuma et al. | |
| 5,132,171 A | 7/1992 | Yoshizawa et al. | |
| 5,798,410 A | 8/1998 | Walther et al. | |
| 6,130,274 A * | 10/2000 | Song et al. | 523/411 |
| 6,448,321 B1 | 9/2002 | Tokita | |
| 6,541,105 B1 | 4/2003 | Park | |
| 6,986,941 B2 * | 1/2006 | Morita et al. | 428/318.6 |
| 2001/0027218 A1 * | 10/2001 | Stern et al. | 516/10 |

FOREIGN PATENT DOCUMENTS

| | | |
|---|---|---|
| EP | 0526872 A1 | 2/1993 |
| GB | 1390180 A1 | 4/1975 |
| WO | WO-9315132 | 8/1993 |
| WO | WO-9852997 | 11/1998 |
| WO | WO-0180916 A2 | 11/2001 |
| WO | WO-0218482 A2 | 4/2002 |
| WO | WO-2004005383 A1 | 1/2004 |

OTHER PUBLICATIONS

Roussy, M.G., et al., Governing Electromagnetic and Thermal Field Relations, Foundations and Industrial Applications of Microwaves and Radio Frequency Fields: Physical and Chemical Processes, 1994, pp. 3 & 4, Wiley, New York, N.Y.

* cited by examiner

*Primary Examiner*—Mark Eashoo
*Assistant Examiner*—Melissa Winkler

(57) ABSTRACT

Aqueous-based, dispersed olefin polymers, froths, durable, open-cell foam compositions, structures and articles derived from same; methods for preparation of such froths and foams; and use of the dry durable foams in various applications are disclosed. Further described is use of the foams and structures and articles made of same in absorption, filtration, insulation, cushioning and backing applications, and in particular for odor removal, hygiene and medical applications due to, among other properties, good absorption capabilities, softness and/or flexibility of the foams and their recyclable nature.

9 Claims, 1 Drawing Sheet

FROTH AND DURABLE FOAM OF DISPERSED OLEFIN POLYMERS, METHODS OF MAKING FOAM AND ARTICLES PREPARED FROM SAME

BACKGROUND

Hydrophilic, open-cell foams find utility in products for acquiring and distributing aqueous fluids; for example: diapers, adult incontinence pads and briefs, feminine hygiene products, wiping towels and sponges, wound dressings and surgical sponges, and other analogous aqueous fluid-absorption uses. Additionally, both hydrophobic and hydrophilic, open-cell foams may find use in numerous other applications, for example fluid filtration, insulation applications, e.g., sound absorption or sound deadening and heat or cold insulation or barriers, cushioning, carpet and fabric backing.

The invention pertains to mechanically frothed compositions comprising aqueous-based, dispersed olefin polymers; recyclable, durable, open-cell foam compositions, structures and articles derived from same; and methods for preparation of such froths and foams. It further pertains to use of the dry durable foams in the absorption, filtration, insulation, cushioning and backing applications by virtue of, among other properties, their good absorption capabilities, softness and/or flexibility and their recyclable nature.

Mechanically frothed derived foam useful in articles for acquiring and distributing aqueous fluids have been prepared from polymeric latex; for example, carboxylated styrene-butadiene latex-derived foams described in U.S. Pat. No. 4,990,541 and WO-01/80916A2.

Aqueous dispersions of linear olefin copolymers, useful for preparing doctored film coatings are made, but apparently not frothed, using a stabilizing and emulsifying amount of surfactant as described in U.S. Pat. No. 5,798,410.

SUMMARY OF THE INVENTION

The invention comprises aqueous-based, dispersed olefin polymer froths; open-cell, durable foam compositions (dry) derived from same; methods for preparation of such dispersed olefin polymer froths and durable foams; and the use of the durable foams in various applications. The relative softness and flexibility of the foams and their good aqueous fluid absorption and aqueous fluid-wicking capability makes them of particular usefulness in absorbent hygiene articles having, among other properties, fluid absorption and wicking capabilities.

We have discovered an open-cell foam that is prepared from aqueous-based dispersed olefin polymer froth and exhibits high Absorbency Capacity ("AC") (expressed as g of synthetic 0.9 wt. percent saline solution absorbed per g dry foam) of greater than 10 g/g, preferably greater than 15 g/g. The durable foam of the invention preferably is hydrophilic and for selected applications is capable of vertically wicking the described 0.9% saline solution to a height preferably of greater than about 5 cm (~2 in), more preferably greater than about 8 cm (~3 in), even more preferably greater than about 10 cm (~4 in), and most preferably to greater than about 15 cm (~6 in). Vertical wicking ability is measured by a test of Vertical Wicking Height ("VWH"), described in greater detail below.

Also disclosed is an aqueous dispersion comprising the resultant combination of a semi-crystalline, thermoformable olefin polymer; a long chain fatty acid of greater than 18 carbon atoms, deionized water, and a base, wherein the dispersion has a solids content of about 67 weight percent.

The aqueous-based, dispersed olefin polymer froth is prepared from a semi-crystalline, thermoformable polymer (Polymer) which provides an added advantage of imparting a recyclable character to the resulting durable foam itself and to articles that incorporate it. In the case of sound and thermal insulation and cushioning applications, in particular, this makes it a very attractive material from which to fabricate articles, e.g., automobile seat cushioning, headliners and sound insulation components, carpet backing for autos or homes, furniture cushioning and mattresses and padding, gas or liquid filtration devices and similar applications. In such uses it is highly desirable to have an olefin polymer, open-cell foam element that can be easily recycled.

The Polymer is selected from copolymers and interpolymers of ethylene and/or propylene and other monomers selected from $C_4$ to $C_{10}$ olefins, preferably alpha-olefins, and more preferably selected from n-butene, n-hexene and n-octene. The ethylene or propylene content of Polymer ranges from about 2-98 percent of Polymer. The modulus of the durable foam can be controlled by selection of polymers. For example, using a copolymer having a higher level of $C_4$-$C_8$ olefins will give a softer and more flexible foam than a copolymer having lower amounts of $C_4$-$C_8$ olefins. Similarly, a foam made with propylene/$C_4$-$C_8$ olefin copolymer will give a stiffer foam than a corresponding composition made with ethylene/$C_4$-$C_8$ olefin copolymer. Selected comonomer(s) make up the remainder of the Polymer. Further details regarding the Polymer are found below.

The absorbent, open-cell Foam composition of the invention is a durable Foam. It results from drying of the aqueous, frothed dispersion of Polymer under conditions selected to inhibit the coalescence of the individual gas bubbles in the Froth for a time period sufficient to allow dispersed Polymer particles contained in the thin aqueous layer surrounding the entrapped air bubble to fuse before the aqueous film structure undergoes significant collapse. Drying occurs as the water evaporates from the bubbles' surfaces and from the channels or interstices between the bubbles.

Some preferred modes of use and articles comprised of the absorbent Foam include aqueous-fluid absorbent, conformable hygiene articles, more particularly baby diapers, adult incontinence products, feminine hygiene products, nursing pads, sweat bands, wiping toweling and sponges, wound dressing pads, surgical sponges, medical garments, surgical drapery and food packaging absorbent padding. Such padding typically is employed for absorbing meat juice and drippings at the bottom of food packaging trays. The foam is also useful in articles used for timed-release delivery systems, for example as in sustained delivery of pharmaceutical and drug products, as through skin contact patches and the like.

The invention further comprises recyclable, absorbent articles. In the case of generally non-disposable articles of a more permanent and reusable character, such as sound and thermal insulation and cushioning applications, in particular, the recyclable nature makes the absorbent Foam a very attractive material from which to fabricate articles. This is due to their impact-absorption, sound absorption or other absorption-related properties; for example, in automobile seat cushioning, headliners and sound insulation components, carpet backing for autos or homes, furniture cushioning and mattresses and padding, gas or liquid filtering devices and similar applications.

DETAILED DESCRIPTION OF THE INVENTION

Figure 1:
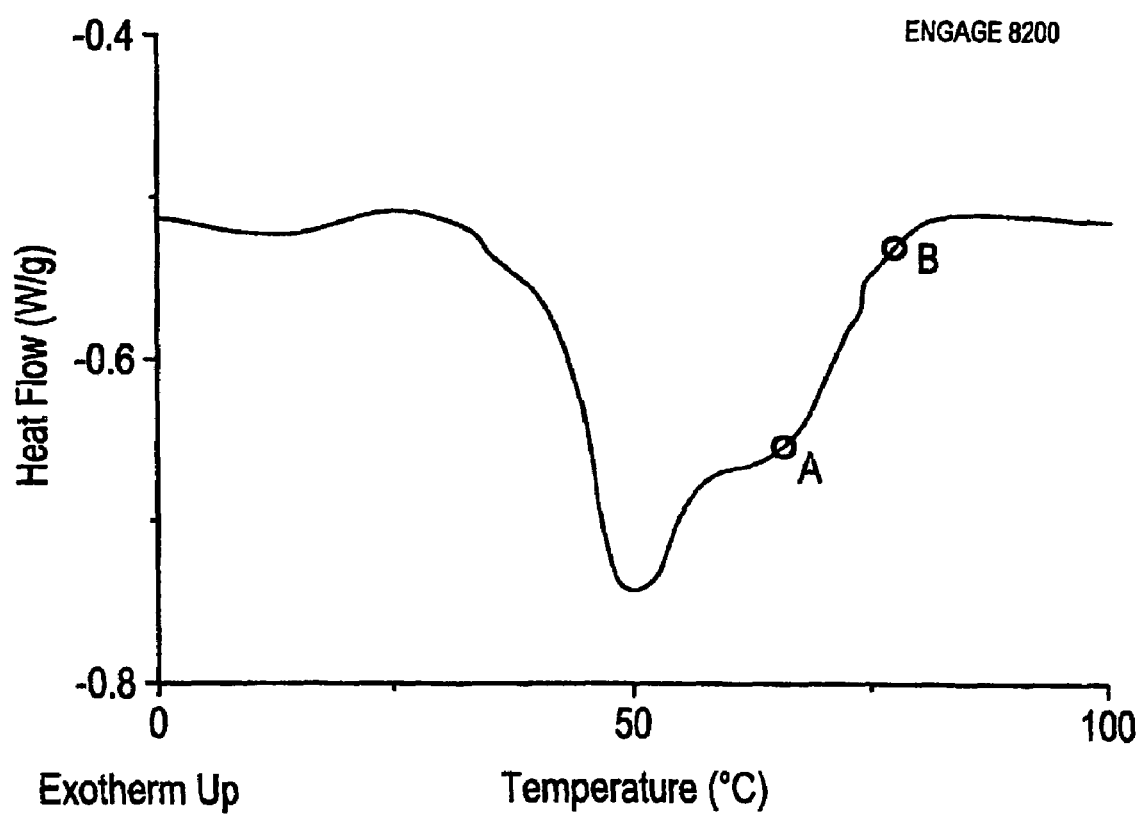
FIG. 1 represents a melting curve, heat flow in watts/gram (W/g) plotted against temperature (in deg Celsius) on the x-axis, obtained by first heat differential scanning calorimetry (DSC) for the ethylene copolymer designated as Polymer 1D in Table-1 and elsewhere. The endotherm plot of a DSC curve may be used to determine an approximate melting temperature range for the respective Polymer, as well as to determine the temperature ($T_{x\%c}$) for a given percentage of Polymer residual crystallinity, as described more fully and utilized for purposes noted below.

All percentages and parts, unless otherwise stated, are expressed by weight.

Definition of Terms

The term Conformable as used here means the ability to bend and flex to the shape desired by the user; for example, the shape of a wearer of an absorbent article. The term Dispersion as used here means a two phase liquid/polymer composition where the aqueous phase is normally the continuous phase and the Polymer is suspended therein in a stable fashion, suitably with the aid of a dispersing agent/dispersant so that the polymer will remain dispersed at least for as long as it will require to complete the frothing step. Preferably the polymer will remain dispersed throughout the entire frothing and drying process so that a complete process can be conducted, either batch-wise or in a continuous fashion, without the polymers settling out of the dispersion. Suitable methods are taught in the art; see for example U.S. Pat. Nos. 5,798,410 and 6,448,321.

The term Drying as used here means a process of causing a Froth to become a Dry Foam and the term Dry as used herein means elimination of at least 95 percent of the water from the Froth.

The term Frothing or Frothed as used here means a process of incorporating substantial volumes of air, or other gas, in a liquid where at least 80, preferably at least 85 and more preferably at least 90 volume percent of the frothed material consists of the gaseous component. It is understood that the aqueous liquid can be a molecular solution, a micellar solution or a dispersion. In general the froth is created by mechanical methods such as high shear mixing under atmospheric conditions or optionally injecting gas into the system while mixing.

The term Froth as used here means an aqueous dispersion of the Polymer which has been Frothed, as described above, before Drying.

The term Foam as used here means a durable structure having an open cell content of at least 80% or greater, preferably at least 85% or greater and more preferably at least 90 percent or greater, as determined by and according to ASTM D2856-A.

The term Major Surface as used here means, in a Foam, one of two substantially parallel surfaces of largest area, in contrast to a minor surface thereof. While possible to cut and trim a raw foam in a manner to form a six surface, regular three dimensional cubical geometrical structure, where all six Foam surfaces are of substantially the same area, because of the practical nature of continuously generating a foam article, it's normally accomplished by spreading frothed material on a conveyer moving in the x-direction, of y-dimension Froth width, and z-dimension Froth thickness. The z-axis or z-direction means the axis substantially perpendicular to the xy-plane defined by the surface of such a conveyor and therefore generally perpendicular to a Major Surface of the Foam as generated. Two major Froth surfaces of x-length and y-width, which when dried to Foam results in a three dimensional Foam structure of surface area equal to about xy on both the top and bottom. It is each of these top and bottom Foam surfaces that are referred to here as a Major Surface, or in the case of Foam that has been slit into pieces of approximately equal thickness along the x-y axes, Major Surface means the resulting larger parallel surface on each opposite, parallel side of each of the resulting slit sheets of Foam.

Olefin Polymers

The semi-crystalline olefin polymer (Polymer) is selected from copolymers and interpolymers of ethylene and/or propylene and other monomers selected from $C_4$ to $C_{10}$ olefins, preferably alpha-olefins, more preferably from $C_4$ to $C_8$ alpha-olefins and most preferably selected from n-butene, n-hexene and n-octene. The ethylene or propylene content of the Polymer ranges from about 2-98 wt. percent of Polymer. Where a softer, more flexible foam is desired a primarily ethylene-based polyolefin is selected in which ethylene comprises from about 98 to 65 percent of Polymer. Where a stiffer foam of greater flexural modulus is desired, a primarily propylene-based polyolefin may be selected, propylene comprising from about 98 to 65 percent of the Polymer. Selected comonomer(s) make up the remainder of the Polymer.

The Polymer has the following characteristics and properties:

1) Crystallinity as determined by the observance of at least one endotherm when subjected to standard differential scanning calorimetry (DSC) evaluation (see for illustration purposes, FIG. 1);

2) for ethylene-based Polymers a melt index ("MI") determined according to ASTM D1238 at 190 deg C. (375 deg F.) with a 2.16 kg (4.75 lb) weight (i.e., condition 190 C./2.16 kg) of about 30 or less, preferably of about 25 or less, more preferably of about 22 or less, and most preferably of about 18 g/10 min or less and about 0.1 or greater, preferably about 0.25 or greater, more preferably about 0.5 or greater, and most preferably about 0.75 g/10 min or greater; and for 1-propene-based Polymers a Melt Flow Rate ("MFR") determined according to ASTM D1238 at 230 deg C. (446 deg F.) with a 2.16 kg (4.75 lb) weight (i.e., condition 230 C./2.16 kg) of about 85 or less, preferably of about 70 or less, more preferably of about 60 or less, and most preferably of about 50 g/10 min or less and about 0.25 or greater, preferably about 0.7 or greater, more preferably about 1.4 or greater, and most preferably about 2 g/10 min or greater.

3) for ethylene-based Polymers a density of about 0.845 or greater, preferably about 0.85 or greater, more preferably about 0.855 and most preferably about 0.86 g/cc or greater, and about 0.925 or less and preferably about 0.91 g/cc or less, more preferably about 0.905 or less, and most preferably about 0.90 g/cc or less; and for 1-propene-based Polymers because density is a less commonly used measure of the backbone composition than for ethylene Polymers, a 1-propene based Polymer comprises about 5 percent or greater, preferably about 7 percent or greater and about 35 percent or less, preferably about 25 percent or less comonomer content.

One class of Polymers particularly suited to use in the invention are copolymers of ethylene and 1-octene or 1-butene, where ethylene comprises from about 90 or less, preferably about 85 or less to about 50 or greater, preferably about 55 or greater, and 1-octene or 1-butene from about 10 or greater, preferably about 15 or greater to about 50 or less, preferably to about 45 or less percent by weight of the copolymer, and that have Melt Index of about 0.25 or greater, preferably about 0.5 or greater and about 30 or less, preferably about 20 or less g/10 min.

Another particularly preferred class of Polymers for use in the invention are copolymers of 1-propene and ethylene, 1-octene, 1-hexene or 1-butene, where 1-propene comprises from about 95 or less, preferably about 93 or less to about 65 or greater, preferably about 75 or greater, and ethylene, 1-octene, 1-hexene or 1-butene comprise from about 5 or greater, more preferably about 7 or greater to about 35 or less, preferably 25 or less percent by weight of the copolymer, and that have a Melt Flow Rate of about 0.7 or greater, preferably about 1.4 g/10 min or greater and about 85 or less, and preferably about 55 g/10 min or less.

Alternatively, instead of a single Polymer a blend of polymers may be employed that has the physical characteristics described above. For example, it may be desirable to blend a first polymer with relatively high MI or MFR that is outside the range described above, with another of relatively low MI or MFR, so that the combined MI or MFR and the averaged density of the blend fall within the ranges noted above. A more crystalline alpha-olefin polymer may be combined with one of relatively lower crystallinity, such as one having a significant amount of long chain branching, to provide a blend that has substantially equivalent processing capability in preparing stable Froth and durable Foam of the invention. Where reference is made to a "Polymer" in this specification, it is understood that blends of olefin polymers with equivalent physical characteristics may be employed with like effect and are considered to fall within our description of the invention.

A particularly preferred class of Polymer when used without other polymers or film forming additives, is characterized by exhibiting a particular type of DSC plot of the Polymer's endotherm. In the preferred class, the observed endotherm exhibits a relatively gentle slope as the scanning temperature is increased past the final endotherm maximum (i.e., the last inflection point on the DSC curve, e.g., point A found on FIG. 1., where the curve slope becomes positive and the curve then returns to baseline state). This reflects a polymer of broad melting range rather than a polymer having what is generally considered to be a sharp melting point.

Consequently, the drying temperature of Froth prepared from such a preferred Polymer can be more easily maintained at or near a point (e.g., point B on FIG. 1.) on the endotherm curve a significant distance from the return to baseline temperature at which point a major part, but not all, of the crystalline portions the Polymer are melted and allow the remaining Polymer particles to fuse or coalesce via their amorphous regions. In that fashion, by maintaining such a temperature during the Froth drying process most of the Polymer is allowed to fuse without a complete loss of Polymer crystallinity and resultant tensile strength, and the bubble collapse that would otherwise ensue, if all crystalline portions of the Polymer were to be melted quickly. One method to determine the maximum temperature at which to conduct Froth drying that is below the point where such a loss of tensile strength would occur, is to calculate a temperature ($T_{x\%c}$) where approximately x % residual crystallinity remains in the selected Polymer. For a given Polymer, the factor used to convert specific heat of melting into nominal weight percent crystallinity in that Polymer can be determined from the melting endotherm (as represented by a DSC curve) for that Polymer. For the ethylene-based polymer designated as Polymer 1D in Table-1, a typical first melt endotherm plot is represented by FIG. 1. To prepare a sample for DSC analysis, a Polymer or Polymer foam sample may be compression molded by first heating sample to a temperature great enough to eliminate all crystallinity (about 190 deg C. for ethylene-based Polymer and about 230 deg C. for propylene-based Polymer), and then cooling in the compression mold at a rate of 10 deg C./min. Prior to the DSC analysis the compression molded sample is then aged for at least two days, and preferably at least a week, at room temperature. The DSC endotherm is, likewise, generated using a heating rate of 10 deg C./min. The factor used to convert specific heat of melting into nominal weight percent crystallinity for an ethylene-based polymer is 292 joules/gram (J/g)=100 wt % crystallinity. From the endotherm plot, a specific heat of melting $\Delta H_m$ of the Polymer in J/g can be determined by integrating the area between the endotherm plot and the baseline. With the noted factor, the total crystallinity of a sample (units: wt % crystallinity) is calculated as 100% times $\Delta H_m$ divided by 292 J/g. Using this conversion factor, 1% residual crystallinity corresponds to 2.92 J/g, 2% corresponds to 5.84 J/g, and so forth, for ethylene-based polymers.

Accordingly, using this relationship, for the Polymer represented in the DSC of FIG. 1, $T_{x\%c}$ is defined by the temperature at which heat of melting on the higher temperature side of the perpendicular dropped to the baseline at that temperature corresponds to x % crystallinity. Such calculations (often referred to as partial area calculations) are easily done using standard software supplied with a DSC instrument. Hence, $T_{1\%c}$ refers to the temperature, determined from the first heat DSC endotherm by partial area calculation using perpendicular drop to the base line, at which 1% crystallinity (e.g., 2.92 J/g for ethylene-based copolymer) is obtained. For a propylene-based polymer, a factor of 165 J/g is substituted in similar fashion and used to calculate the residual crystallinity of the polymer at a specific temperature on the endotherm represented by its respective DSC first heat plot. To provide adequate residual crystallinity and tensile strength and avoid Froth bubble collapse when drying, one would suitably operate at $T_{x\%c}$ on the DSC plot that represents greater than about 1, preferably greater than about 1.5 and more preferably greater than about 2 weight and suitably less than about 5, preferably less than about 4 and more preferably less than about 3 weight percent, residual Polymer crystallinity, or roughly somewhere in the region between about point A and point B on the plot of FIG. 1. If a blend is to be used, for example a blend of propylene-based polymer with an ethylene-based polymer, the polymers will normally be immiscible or partially miscible and one polymer becomes the continuous phase and the other the non-continuous phase. To determine an appropriate drying temperature range, it is the properties of the continuous polymer phase that one then measures, using the same DSC partial area calculation as described above, to determine a desired $T_{x\%c}$.

Dispersing Agents (Dispersants)

The Dispersant is employed in an amount of more than about 1%, preferably more than about 2%, and more preferably more than about 3%; up to an amount less than about 10%, preferably less than about 8%, and more preferably less than 5%, based upon the weight of the aqueous dispersion of the Polymer.

The Dispersant used to create the relatively stable, aqueous dispersion of Polymer particles in the invention will vary by the nature of the Polymer employed. The same or a different Dispersant may be used to serve as the frothing surfactant in the subsequent preparation of the Froth.

Suitable Dispersants for the Polymer are salts of fatty acid(s) of carbon chain length of greater than 12 and preferably from 18 to 36 carbon atoms. The salts are suitably alkali metal or ammonium salts of the fatty acid, prepared by neutralization of the acid with the corresponding base, e.g., NaOH, KOH, and $NH_4OH$. These salts may be formed in situ in the dispersion step, as described more fully below. The appropriate fatty acid Dispersant is selected to serve as Dispersant for the extrusion melt step in order to attain the desired average particle size of the Polymer, suitably between about 0.2-25 microns and preferably between about 0.5-10 microns. Routine experimentation can determine the type and quantity of Dispersant that provides a dispersion of the desired average particle size.

Frothing Surfactants

Creating and stabilizing the Froth during the frothing and drying step is suitably accomplished by addition of a frothing surfactant to the aqueous dispersion of the Polymer when initially creating the Froth. In addition these surfactants can be used to improve aqueous wetting, if desired. Suitable frothing surfactants are selected primarily from but are not limited to, cationic, nonionic and anionic surfactants. Anionic surfactants are preferred.

Cationic surfactants such as primary amine salts, diamine salts, quaternary ammonium salts and ethoxylated amines and the like may be used, as may nonionic surfactants such as alkylphenol ethoxylates, linear and secondary alcohol ethoxylates of alkyl group containing more than 8 carbon atoms.

Anionic surfactants to be used in preparation of the Froth from a previously created Dispersion of the Polymer are suitably selected from carboxylic acid salts and ester amides of carboxylic fatty acids, preferably fatty acids comprising from 12-36 carbon atoms, e.g., stearic or lauric acid, palmitic, myristic, oleic, linoleic, ricinoleic, erucic acid and the like. More preferred are those fatty acids comprising from 12-24 carbon atoms, particularly their alkali metal (most preferably sodium or potassium), alkanolamine or ammonium salts. When a good "hand" or fabric like feel is desired in the finished Foam, a saturated fatty acid derivative (e.g., the salt of stearic or palmitic acid) is preferably employed. Other suitable anionic surfactants include alkylbenzene sulfonates, secondary n-alkane sulfonates, alpha-olefin sulfonates, dialkyl diphenylene oxide sulfonates, sulfosuccinate esters, isethionates, linear alkyl (alcohol) sulfates and linear alcohol ether sulfates. It is understood that these frothing surfactants may or may not be different than those used to prepare the dispersion. These surfactants serve both to assist in Froth formation and help to stabilize the Froth. The most preferred frothing surfactants, when required, are the alkali metal (more preferably sodium or potassium), mono-, di- and tri-alkanol (more preferably mono-, di- or triethanol) amine and ammonium salts of lauryl sulfate, dodecylbenzene sulfates, alcohol ethoxy sulfates, isethionates, and the dibasic salt of N-octyldecylsulfosuccinimate, as well as mixtures of same.

Dispersion Step

The selected Polymer is dispersed in water, suitably by adding the Polymer and the selected Dispersant(s) in the desired amounts, and in a metered fashion, to the hopper of a bi-axial, polymer extruder where they are melt-kneaded at a temperature of about 220 deg C. (about 430 deg. F.). Preferably, when using an ethylene-based olefin Polymer, a long chain fatty acid of greater than 18 carbon atoms is melt-kneaded with the Polymer. Then deionized water and base (e.g., KOH) sufficient to form in situ the fatty acid salt of Dispersant, are added at about 165 deg. C. (~330 deg F.) to the melt under a pressure of at least 410 psi (~2,800 kPa) to produce the Dispersion. Pressure within the extruder barrel is maintained above the saturated steam pressure of roughly 20 to 35 atmospheres (~2,000 to ~3,500 kPa) to avoid "blow-back" through space between the barrel and screw of the extruder, by ensuring that space is essentially full of the Dispersion. Then the Dispersion is diluted with deionized water at a separate port downstream in the extruder barrel at about 193 deg C. (~380 deg F.) and at about 14 atmospheres (~1,400 kPa) to produce a final Dispersion of about 67 percent solids. Dispersion is conducted from the extruder and collected, after passing through a mild cooling zone to prevent flashing of the water from the Dispersion, at a temperature of about 94 deg C. (~200 deg F.).

Froth Preparation

A froth is prepared from the Dispersion of the Polymer by using a high shear, mechanical mixing process to entrain air or another gas in the aqueous phase of the Dispersion. The amount of air or other gas (where a gas in addition to or other than air is desirable) to be incorporated in the Froth suitably comprises at least 80, preferably at least 85, and more preferably at least 90 percent by volume of the resultant Froth. In general, all components to be used in making the froth are mixed together with mild agitation to avoid entrapping air. Once all of the ingredients are well mixed, the composition is exposed to high shear mechanical mixing. During this step the bulk viscosity increases as more air is entrapped within the continuous aqueous phase. The mixture is mixed until a non-flowable, stiff froth is formed. This generally produces a froth with density of less than about 100 g/L. The time to reach this stage varies with amount and type of frothing surfactant and the amount of mechanical shear. Any mechanical mixing device capable of whipping air into a thickened aqueous dispersion, such as a kitchen blender/hand mixer, Hobart mixer fitted with a wire whip or on a larger scale a Cowie-Riding Twin Foamer (Cowie Riding Ltd., G.B Patent 1,390,180). The commercial foamers also allow one to inject air into their high shear mixing head to obtain very low (less than 50 g/L) density Froth.

Additives

The Foam of the invention may contain filler materials in amounts, depending on the application for which they are designed, ranging from about 2-100 percent (dry basis) of the weight of the Polymer component. These optional ingredients may include, but are not limited to, calcium carbonate, titanium dioxide powder, polymer particles, hollow glass spheres, polymeric fibers such as polyolefin based staple monofilaments and the like. Foam designed for use in the absorbent articles may contain bulk liquid-absorbing material, such as short cotton fiber or other cellulose fiber evenly distributed throughout the polymer foam. Although they are not typically blended with the Polymer dispersion before frothing, due to their strong water absorbent nature, fine particles of super absorbent polymer ("SAP") a lightly cross-linked acrylate polymer, can be evenly distributed upon the surface of the Froth just as it is entering the drying process to provide a durable Foam with extra absorbent properties on that surface when dried. However, if SAP particles are treated (e.g., with a surface layer of delayed water-solubility polymer such as, for example, a hydroxypropyl alkylcellulose ether or a polyoxyethylene resin), to reduce the particles' initial rate of water absorbency until after the Froth has reached the dry Foam state, such "retarded-absorbency" SAP particles may beneficially be added directly to the Polymer dispersion before frothing is initiated.

Other Foam end-uses such as cushioning, particularly flooring backing, can benefit from the addition of low cost fillers such as calcium carbonate or titanium dioxide powder, and similar inert fillers such as polymeric staple fibers. Such additives and fillers can enhance the physical strength and/or the appearance of the resultant composite Foam after drying, as well as to retain or to increase the Foam's impact or other absorption capabilities. For example, about 1-25% such cellulose fiber material of fiber length of about 0.25-35 mm (about 0.01-1.6 in) and preferably of about 0.5-30 mm (about 0.02-1.2 in), may be added without substantial detriment to the absorption performance or structural integrity of the Foam and in fact do enhance durability and structural integrity of the Foam. For some Foam applications, it may be desirable to incorporate one or more antioxidants and/or other stabilizing agents to enhance the resistance of the Foam to oxidization and yellowing from exposure to harsh conditions and weathering.

Synthetic latex polymers (e.g., styrenic or acrylic lattices) and/or other film-forming polymers may also be utilized as additives to the Froth to form stable and durable Foams and may aid in processing of the Froth and conversion to Foam by contributing to enhanced coalescence of the Polymer particles at both lower and higher drying temperatures. If utilized, such lattices or other film-forming polymers are suitably employed at levels of about 10-40 percent, dry weight basis, of the Polymer. When additives are to be incorporated in the Foam, they are suitably added in the specified amounts to the dispersion of the Polymer before the Froth is prepared in the frothing step. However, as previously noted above, when water soluble or highly hygroscopic additives (such as SAP) are desirable to add, they are added to the Froth surface immediately before the drying step or are injected into the finished durable Foam.

Another additive that is preferably included in the Foam is an odor adsorptive agent, such as activated charcoal, to impart odor absorbing properties to the Foam. The Foam can then be utilized in various applications where such properties are useful, for example in personal hygiene absorbent articles, shoe sole inserts, air filters and the like. The adsorptive agent is suitably utilized in a particulate form that is physically incorporated into the Froth and ultimately in the finished Foam. The Foam can be appropriately molded or cut to obtain articles of various shapes to fit the use intended. By way of example, when activated charcoal is employed, the particles are distributed uniformly throughout the Froth, suitably by mechanical mixing into the Dispersion and retain such distribution in the finished Foam. The average size of adsorptive particles will be selected both for the maximum adsorption effect as well as their ability to remain uniformly distributed in the Froth before fully dried to form the Foam. Suitable average particle size for activated charcoal is from about 1 micrometer to about 600 micrometers, preferably greater than 10 micrometers, more preferably greater than 100 micrometers and preferably smaller than 400 micrometers, more preferably smaller than 200 micrometers. The amount of activated charcoal to be dispersed will be selected according to the end use, but typically is from about 2 to about 18 wt. percent based on dry polymer solids in the Dispersion; preferably the amount used will be greater than 4, more preferably greater than 8 percent and preferably less than 12, more preferably less than 10 percent. Optimum amounts of other adsorptive materials can be determined by simple trial and error experimentation, but excessive amounts may cause excessive Froth density or bubble collapse and are to be avoided.

Froth Stabilization Agents

Water-soluble, film-forming natural and synthetic polymers such as those selected from alkylcellulose ethers, hydroxyalkyl cellulose ethers and hydroxyalkyl alkylcellulose ethers, e.g., methylcellulose; hydroxypropyl methylcellulose (HPMC); hydroxyethyl methylcellulose (HEMC); hydroxyethyl cellulose (HEC); hydroxypropyl hydroxyethylcellulose (HPHEC) and hydroxypropylcellulose (HPC), polyoxyethylene (water-soluble, high molecule weight polymers of ethylene oxide, preferably of about 20,000 molecular weight or higher, such as POLYOX resins); natural products such as guar gum, xanthan gum and similar water-soluble thickening agents, will serve as stabilization agents ("Stabilizers") for the frothed Polymer dispersion. From about 0.05, preferably about 0.1, and more preferably about 0.2 percent, to about 2 percent preferably to about 1, and more preferably to about 0.5 percent of stabilizer, based on the dry weight of the Polymers.

Treatment Equipment and Process Conditions

The Froth and Foam of the invention may be prepared using any suitable equipment normally employed for frothing of aqueous liquids and dispersions and drying of such froths. Any mixing or stirring device useful for preparation of aqueous particulate dispersions can be utilized in preparation of the dispersion and in subsequent formulation and blending with surfactants and other additives, with care being taken to avoid entraining significant amounts of air in the blend before frothing commences. A kitchen blender or other bladed mixing equipment is such a suitable device. When the blend is prepared, the same or different mixing device can then be operated to commence air entrainment in the formulated aqueous blend containing the Polymer and other additives. A specifically designed frother such as a Cowie-Riding twin foamer may be used to prepare the Froth, so that the desired target 80-90 or 95 vol. % air content of the Froth, depending on the desired density of the final Foam, may be attained. The correct amount of frothing and air content can be easily determined by a few simple experiments. Froth density is measured by drawing off samples of the Froth in cups of predetermined volume and weight, weighing the Froth-filled cup and then calculating the density of the sample. In commercial frothers, air can be added directly into the mixing head to assist in development of low density Froth. The speed of the frothing device can be increased or decreased to attain a desired Froth density.

Drying of the Froth to form the desired Foam may be conducted in batch or continuous mode. Devices such as conventional forced air drying ovens or banks of infrared heating lamps or dielectric heating devices, e.g., radio (typically operated at permitted frequency bands in the range between 1-100 megaHertz) and microwave (typically operated at permitted frequency bands in the range between 400 to 2500 megahertz) frequency energy generating sources, lining a tunnel or chamber in which the Froth may be placed or conveyed through, in a continuous fashion, may suitably be employed for drying. A combination of such drying energy sources may suitably be employed, either simultaneously or sequentially applied, to dry Froth to form Foam. The simultaneous use of a dielectric device and a forced air drying oven is a preferred mode of operation, and for Foam on the order of a quarter inch (~0.6 cm) thickness the drying can be achieved as quickly as 45-90 seconds when the forced air oven is operated at approximately 75 deg C. and a radio frequency generator heats the Froth to an internal temperature of about 45-50 deg. C. The temperature of the Drying operation is selected according to the nature and the melting range of the Polymer (as determined by DSC) employed to prepare the Foam, as described immediately below. The dielectric heating frequency bands, permitted for industrial use in various countries, are designated in greater detail in the reference "Foundations of Industrial Applications of Microware and Radio Frequency Fields", Rousy, G and Pierce, J. A. (1995).

Driving and Recovery Steps

Foam is suitably prepared by removing the liquid/aqueous element of a Froth prepared in the manner of the invention teaching. Desirably the amount of froth volume collapse during this conversion is to be minimized. Generally, Foams will have volume losses of not greater than about 30% during the drying process. The Froths of the invention are dried and converted to invention Foams suitably by heating them in a forced air drying oven, at temperatures selected for optimum drying. Typically the Froth is heated to a temperature between about 60 and 120 deg C. (~140 and 250 deg F.). As the nature of the Polymer permits, processing is conducted at the highest temperature feasible to remove water as rapidly as possible from the Froth without destroying the viscosity of the Polymer on the surface of the bubbles of the Froth or causing significant (e.g., more than 30 volume percent) collapse of the partially dried froth. Typically, it is desirable to perform the drying step at a temperature that approaches, but does not exceed the Polymer's melting range. The desired condition is to attain a temperature where the amorphous regions in the Polymer can begin to coalesce while the pseudo-crosslinkings in the Polymer, created by the crystalline regions in same, are still capable of imparting sufficient viscosity to the heated Polymer to avoid or at least minimize collapse of the Froth before the Foam has become fully "dried" in its ultimate form and dimension and at least 95 weight percent of the water in the Froth has been driven out.

The melting range of a Polymer is determined by Differential Scanning Calorimetry (DSC) techniques, and the temperatures bracketing the region of the DSC endotherm, or the final endotherm if more than one exist, just before a return to baseline on the DSC scan plot is the temperature range in which drying of the Froth to form the finished Foam is to be conducted. As described earlier the particularly preferred Polymers, when used without other polymers or additives, are characterized by exhibiting a specific desirable DSC plot of their endotherm(s).

In such Polymers, the desired endotherm exhibits a relatively gradual positive slope as the scanning temperature is increased past the final endotherm maximum (i.e., the last inflection point, as represented by point A on the curve in FIG. 1, on a DSC curve where the curve slope then becomes positive and the curve returns to baseline state). This reflects a polymer of broad melting range rather than a polymer having what is generally considered to be a sharp melting point. Consequently, the drying temperature for a Polymer is best maintained at or near a point (e.g., represented by point B on FIG. 1) on the endotherm curve a significant distance from the return to baseline position at which point a major part, but not all, of the crystalline portions the Polymer fuse and Polymer particles fuse/coalesce. During the Drying process, by maintaining such a temperature, most of the Polymer is allowed to fuse without a complete loss of Polymer tensile strength and the bubble collapse that would otherwise ensue, if all crystalline portions of the Polymer were to be melted quickly.

When Drying is to be conducted with a dielectric heating source (e.g., microwave generator), it is desirable to ensure that the liquid used to provide the aqueous element of a Froth contains at least a trace amount of ionic material. This can be accomplished by use of an ionic surfactant as the Dispersant or frothing surfactant or by adding a small amount (e.g., 100 ppm) of water soluble alkali metal electrolyte salts, such as sodium acetate, potassium bicarbonate or the like, to the Dispersion prior to or during Frothing.

When a blend of Polymer with additives (including blends with other thermoformable polymers) is to be employed in the preparation of invention Froth and Foam, a DSC plot for the blend is first suitably generated. From that plot endotherm(s) of the blend may be observed and, consequently, the final melting range of the blend determined and a suitable drying temperature for converting the Froth to durable Foam selected.

In a preferred method for making the Foam, Froth is continuously doctored onto a conveyor device from which the resultant Foam will be recovered. Alternatively, Froth may be doctored directly onto a substrate to which, when dried, it will adhere to form a laminated structure with the resultant Foam on at least one side of that substrate. If desired, a substrate may be applied to each Major Surface of the Froth providing a resultant Foam "sandwich", or multiple layers of Foam, separated by one or more substrate elements may be readily fabricated by alternating Foam/substrate/Foam/substrate, etc. As a matter of choice, either the Foam or substrate may provide the outer layers of the laminated structure, or one outer layer of each type may be selected, as can readily be perceived and prepared by the artisan. However, the Foam typically can be attached to a desired substrate in any conventional manner, e.g., by mechanical means, by use of adhesives, by heat lamination, etc.

In a particularly preferred method, the Froth is doctored on a continuously moving substrate (or multiple layers of substrate/Froth/substrate, etc. are laid in a continuous fashion) and the Drying step is conducted in a continuous rather than batch fashion. More preferably the Drying step employs at least two energy sources, and which even more preferably are applied in a continuous fashion. Most preferably the at least two energy sources are configured in a manner to allow Drying to be conducted either through a simultaneous or a sequential exposure of the Froth to those drying energy sources.

A particularly preferred embodiment of the invention is to continuously doctor Froth on a substrate, which itself has fluid absorptive properties and to which the Polymer in the Froth may readily bond when heated. Drying then yields a laminated foam structure that creates a cohesive structure comprising two layers of different absorbent materials. A laminate structure with different wicking and/or fluid absorbent capacity properties in each laminate layer is thereby formed from which useful absorbent articles can be fabricated. For example a pre-formed, thermoplastic polymeric foam substrate layer of desired open-cell structure and desired cell size may serve as such a base substrate. Such a substrate layer is preferably made up primarily of the same thermoplastic material as that of which the Froth is mainly comprised.

One means to obtain such a two-layer structure is to prepare a first Froth of the invention, dry it into a resulting Foam and shape appropriately for use as the first substrate layer. Then upon that first Foam substrate, lay down a second (same or different than the first) Froth of the invention and dry the second Froth to form the second Foam layer.

Alternatively, two Froths are prepared and the first Froth is prepared with a sufficient vertical compressive strength, so that the second Froth can be laid on top of the first Froth layer without a significant reduction in the volume of the first Froth layer.

One means to attain sufficient vertical compressive strength in the first Froth layer is to select a first Froth having a density greater than that of the second Froth layer to be laid on it. Another means to attain the desired vertical compressive strength is to partially dry the exposed major surface of the first Froth layer only enough to produce a light skin sufficient to support the weight of the second Froth layer without significant reduction in volume of the first Froth. Both Froth layers are then simultaneously fully dried to Foam, resulting in a two layer Foam laminate structure. In another variant of the invention, the first Foam layer is prepared from an extruded, open cell thermoplastic foam of a material of same or similar nature compatible to that employed in forming the Froth to be laid on the first Foam. Alternatively, the first Foam layer is prepared from a different yet compatible type of open cell Foam (e.g., a polyurethane open cell foam) then a layer of Froth (e.g., a polyolefin open cell froth) is laid upon that first Foam to yield a useful dual layer Foam structure.

In any of the structured, laminate embodiments of the invention, two different layers of Foam having structures of differentiated capillary force, for example two different cell architectures or Foams of different average cell sizes, are preferably selected for the first and second Foams of a laminate structure. Because of the similar or same nature of the Polymer base in the Foam layers, a good bond is formed between them so that a structured laminate is formed which can exhibit a selected absorption and/or wicking property in each layer of the structure due to the different capillary force of the Foam in each layer.

Foam having different cell architectures within it is one preferred embodiment of a structure exhibiting differentiated capillary forces. Such a structure provides a differentiated absorption and/or wicking capability in distinct layers of the structure. The polyolefin/polyurethane dual layer Foam structure noted above, is one example of such a differentiated cell architecture. Another embodiment of the invention, and especially preferred, is a Foam that has a major portion of substantially ellipsoidal cells, and having their major axis generally aligned in parallel fashion to a Major Surface, and lying in an xy-plane, of the Foam. Such Foam may be prepared by subjecting the durable Foam to mild heating while uniformly applying pressure to at least one surface of the Foam in a cell orienting fashion. Preferably the major portion of the surface cells in the resultant Foam become stably formed in a generally ellipsoidal shape, the major axis of such ellipsoidal cells being generally aligned with the xy-plane and roughly parallel to a Major Surface of the Foam.

One method to achieve such ellipsoidal cell shaping and major axis orientation is to subject the durable Foam, preferably just after its drying, to a temperature at the lower end or at least substantially below the upper end of the melting range of its component polymer(s). The Foam is heated to a temperature near the lower end of the melting range, providing sufficient heat to soften at least one surface of the Foam without initiating Foam collapse, while evenly and uniformly applying a modest pressure to that surface. Sufficient heat and pressure is applied to cause the diameter of such cells at least at and near such surface to be shortened along their z-axis, thereby causing them to assume the shape of a "flattened" beach-ball and imparting an ellipsoidal shape to those cells with the major (longest) axis of the three-dimensional cell oriented generally perpendicular to the z-axis and in an xy-plane of the Foam. While cells below the surface of the Foam to which pressure and heat is applied may also be "flattened" into ellipsoids, it is not necessary to do so to more than a depth of about 2 to 25 percent of the initial thickness of the Foam if the Foam is primarily intended for use as a single layer core for both absorption and distribution of fluid in for example a personal hygiene article; i.e., compression of the Foam need only be by about 2, preferably greater than about 5 and more preferably greater than about 7, to less than 25, preferably less than about 20 and more preferably less than 15 percent in thickness. Foams with such compression provide surprisingly enhanced wicking capabilities over those which have not had a significant percentage of their cells reoriented into the ellipsoidal structure. If a Foam is intended primarily for use as a distribution layer/component in an article, greater than 50 percent compression to achieve reorientation of a majority of cells into the ellipsoidal cell shape may be desirable.

In practice, for a polyethylene-based Foam later described in preferred embodiments, the reorientation of cells into ellipsoidal shape is achieved by heating at least one surface to a temperature of from about 40 to about 60 deg C. while applying a suitable pressure. Such a typical suitable pressure (gauge) of from about 240 kPag to about 830 kPag (about 35 to about 120 psig) and preferably of between about 310 kPag to about 620 kPag (about 45 to about 90 psig) provides a Foam with sufficient ellipsoidal cell structure at or near the surface to enhance the vertical wicking capabilities over the same unmodified Foam several fold and, in optimized form, such modified Foams can exhibit a vertical wicking height for 0.9% saline in excess of 8 and even of 10 cm.

While both Major Surfaces of a Foam may be treated to provide ellipsoidal shaped cells it is generally sufficient, when both fluid absorption and distribution attributes are desired in a Foam, to treat only one Major Surface because the primary purpose is to achieve a differentiated absorptive profile on the two opposite Major Surfaces. It may be advantageous to so treat both Major Surfaces simultaneously, if afterwards the Foam will be slit longitudinally and roughly along the median xy-plane between the two Major Surfaces of the Foam, as described in greater detail below, to provide two "half" sheets of Foam with similar adsorptive profiles and cell size and architecture gradients from the original Major Surface to the original center of the Foam layer.

Other substrates with which the invention Foam may be combined to form cohesive articles are preferably made of the same polymer as mainly comprises the Froth or one also capable of readily bonding to it. Illustrative examples of suitable substrates are woven or non-woven fabric; loose substrate structures that are generated in a melt spun-bonding process or a similar melt blown or air laid non-woven structure or one generated by other similar fabrication techniques; a relatively open woven mesh; a cellulosic sheet (e.g., paper, cardboard and the like); a glass fiber insulation batting and derivative sheet articles; thermoplastic film or sheet, such as a diaper or feminine hygiene product backing sheet; a laminated metallized plastic sheet or a film such as used to back an insulation foam material; a carpet backing fabric or mesh, and the like.

If desired, a Froth or multiple layers of Froth may be formed into a shaped profile, by forcing the Froth through a die or other profile-inducing shaped structure, before the drying step is performed. An embossing step may be conducted by application of shaped elements on the conveying belt for the Froth during drying, or later in a separate thermal embossment step by application of a heated, shaped elements-bearing belt or wheel to a major surface of the Foam. In another embodiment, the Froth may be placed in a heated mold form in which channels are provided to conduct generated steam from the Foam to the ambient atmosphere. Molded articles of Foam that have a particularly desired shape can be formed that are then useful in the fabrication of absorbent articles, particularly for hygiene and medical applications where body conformable articles are often desired.

Foam Slitting Step

While Foams of the invention may be utilized directly as laid and dried, particularly in commercial operations where a sheet of Froth and resultant Foam may be continuously produced, it is frequently desired to form a durable Foam of roughly twice the thickness of the Foam to be used in the finished article. Then to slit the Foam along the axis of the direction of continuous flow into two Foam sheets of about the same thickness.

By virtue of the fact that a foam will normally dry more quickly at its outer, exposed surfaces than in the interior of the foam, the size of the open cells on the outer surfaces when dried will normally be smaller than the size of the cells in the interior. This is a result of the fact that there will be a certain amount of bubble coalescence and resultant bubble diameter enlargement during the drying step. The size of the bubbles/final cell size is a function of time required to dry the Froth and for the Polymer particles to merge to form cell walls in the final Foam. The longer the time, the more bubble coalescence will occur, more bubble diameter enlargement will take place and the larger will be the ultimate cell size in the finished Foam. Accordingly, unless a uniform drying throughout the Foam can be accomplished there will be some cell size gradient from the surface to the interior of the Foam as formed. This result is desirable in many applications such as sound insulation, and in absorbent applications where the foam needs to uptake fluid quickly, yet wick fluid away from one surface of foam, e.g., in diapers, adult incontinence articles or feminine hygiene articles, as the ultimate goal. After slitting of the Foam along an xy-plane approximately midway between the Major Surfaces (or "Foam center"), the resulting two pieces of Foam will exhibit the cell size gradient from one surface to the other in a mirrored fashion for each half of the slit Foam sheet. In use of the slit Foam for wicking applications, the Foam is oriented so that the larger cells of one Major Surface will initially contact the aqueous solution to be absorbed and then the capillary action of the increasingly smaller cells traveling toward the other major surface will cause the solution to be wicked away from the first major surface and to be distributed nearer to the second major surface. The result is a dryer surface near the point of initial contact with the Foam, providing the desired effect in such diaper, medical and hygiene applications of the Foam.

For use in absorbent articles, a Foam exhibiting a cell size gradient between the two Major Surfaces is highly desirable, larger cells at one Major surface allowing for a quick uptake of fluid insults and smaller cells at the other Major Surface imparting a wicking action to the Foam element in a final article to move fluid away from the insult site. Suitably, the cell size gradient is such that the major portion of cells fall into a range from about 5, preferably from about 10 microns (micrometers) at one Major Surface of slit Foam to about 1000, preferably about 1100 microns at the other Major Surface. The major portion of cells on one Major Surface is normally found in a range of between about 20 to about 100 microns and the major portion of cells at the other Major Surface to be found in the range between about 200 to about 1000 microns; more preferably said gradient varies from cells ranging between about 30 and about 80 microns at one Major Surface and between about 250 and about 800 microns at the other Major Surface, and most preferably said gradient varies from about 30 microns at one to about 80 microns at the other Major Surface.

Cell size gradient can be influenced by faster or slower drying of the Froth, with slower drying generally resulting in a Foam of wider cell size gradient and faster drying in one of narrower size gradient. Addition of a more effective Froth stabilizer, such as a hydroxyalkyl cellulose ethers, or film-forming additive such as a styrenic latex, may result in a Foam with a narrower cell size gradient as well. Slitting of the Foam layer of a laminated—substrate/Foam/substrate—structure can yield two Foam/substrate laminates, with each laminate of a similar structure. Other variations on this same concept can be readily envisioned by the skilled artisan.

Foam Cell Size and Measurement/Calculation Methods

The size of cells in the durable Foam is determined by first obtaining an image of the cells using a Scanning Electron Microscope (SEM) to provide a black and white image of surfaces or cross sections of the Foam. The SEM image is then subjected to electronic image scanning and the data from the scan is analyzed by SCION imagining software available from SCION Corp. to provide a cell size plot for a given image area. The data may be graphically displayed for further analysis as a function of distance along a chosen axis of the B/W image from which input was collected to visually display the structural nature of the Foam.

Testing Procedures

Unless otherwise indicated, the following test procedures are employed to measure the characteristics/performance of the Foam samples.

Vertical Wicking Height ("VWH") of Foam.

This test is employed to quantify the ability of an open cell to move fluid away from the insult site (i.e., the point of contact by the "insult" fluid to be wicked away). A sample strip of the Foam, approximately 2.54 cm (~1 inch) wide and approximately 30.5 cm (~12 inches) long is adhered to a plastic plate using double-sided tape and positioned adjacent and parallel, in the longer direction, to a ruler or other similar measurement tool such that the bottom of the strip is positioned with the 0 indicator marker on the ruler. The plate with sample is then suspended over a bath of the 0.9% aqueous saline solution that contains a minimal amount of a food coloring (to assist observation of the movement of the fluid front in the foam strip). At time "zero" the bath is raised to just contact the bottom edge of the Foam strip. The height from the bottom edge of the strip, of the fluid front on the strip surface is recorded at selected time intervals, generally at 2, 5, 10, 30 and 60 minutes. For speed and simplicity, VWH after 5 minutes is often measured and reported. In some cases, when the sample strip is less than 30 cm, wicking may exceed the height of the strip. In such cases, the length of the strip is indicated followed by a "+" to indicate that the VWH exceeds the height of the sample.

Absorbency Capacity ("AC")

Absorbency capacity is determined using a pre-weighed (dry weight) foam sample. The sample is fully immersed in a bath of the same 0.9% aqueous test solution. Once fully saturated, it's removed from the bath with tweezers or a spatula. It is placed on a coarse wire mesh where excess fluid is permitted to drain until visible fluid flow from the sample ceases and the saturated Foam sample is weighed to establish the "wet weight". AC is then calculated by dividing the [wet weight-dry weight] difference by dry weight of the strip.

Specific Embodiments of the Invention

All reported percentages are by weight, unless otherwise stated.

Table 1 summarizes the composition and properties of various ethylene copolymers that are useful for preparation of Froth and Foam. Exemplification of ethylene/1-octene and ethylene/1-butene copolymers is described. Examples 1 through 5 demonstrate the dispersion of the Polymer, frothing of the Polymer dispersion, drying of the Froth to form the durable Foam and the ability of the Foam to absorb and wick saline aqueous solutions (e.g. synthetic urine or synthetic blood samples, or "insults").

TABLE 1

Polymer Composition

| Polymer Designation | Ethylene/1-Octene Content (*other) (wt %) | Density (g/cc) | Melt Index ASTM D1283 [190 deg C./2.16 kg] (g/10 min) |
|---|---|---|---|
| 1A | 55/45 | 0.857 | 1 |
| 1B | 58/42 | 0.864 | 13 |
| 1C | 60/40 | 0.870 | 30 |
| 1D | 62/38 | 0.870 | 5 |
| 1E | 65/35 | 0.875 | 3 |
| 1F | 67/33 | 0.880 | 18 |
| 1G | 69/31 | 0.885 | 30 |
| 1H | 78/22 | 0.902 | 30 |
| 1J | 80/20 | 0.902 | 3 |
| 1K | 70/30* | 0.865 | 5 |

*(Ethylene/1-Butene)

EXAMPLE 1

Dispersion

A dispersion of an ethylene/1-octene copolymer is prepared from Polymer 1D (Table I above), a copolymer having ethylene/1-octene content of 62/38 percent (ENGAGE 8200 elastomer which is supplied by DuPont Dow Elastomers), and having a density of 0.870 g/cc and a melt index of 5 g/10 min (as determined by ASTM method D1238 condition 190 deg C./2.16 kg). In the manner described earlier under the heading "Dispersion Step", 10,000 parts of the copolymer is fed into the hopper of the polymer extruder together with 640 parts (active weight) of dispersant (Unicid 350, a dispersant containing a 26 carbon chain fatty acid as active component) and melt-kneaded by a single screw extruder at about 220 deg C. (~430 deg F.). Thereafter into the barrel of the twin-screw extruder 70 parts potassium hydroxide in 850 parts deionized water are added to the polymer/dispersant blend under pressure and a temperature of about 165 deg C. (~330 deg F.). As the blend passes down the extruder barrel, further deionized water is added until a final dispersion of about 59% solids is produced. The resulting dispersion is cooled to about 94 deg C. (~200 deg F.) before exiting the extruder and then recovered.

Froth Preparation

A sample of 196.5 parts of the above-described dispersion (51% active or 100 parts solid Polymer) is blended, in a conventional mixing bowl and taking care not to entrain air while blending, with 3.25 parts of a 30% solution (0.98 part active) of the selected frothing surfactant (sodium lauryl sulfate) and with 8 parts (0.33 part active) of a 2.5% aqueous solution of the hydroxyalkyl cellulose ether Methocel E4M hydroxypropyl methylcellulose thickener supplied by The Dow Chemical Company, into 100 parts deionized water. Small froth samples are prepared with a KitchenAid Professional 9-speed hand mixer (Model KMH9PWH and larger samples are prepared with a Hobart-type stand mixer KitchenAid Professional mixer (Model KSM50PWH) and a pair of wire beaters.

After the initial blend is prepared, air is entrained by mechanical frothing using the same mixers, but fitted with a wire whip and by increasing the mixer speed from medium to high over a period of approximately 5 to 10 minutes, until a stiff froth is formed. Density of the froth is measured by weighing a 3 oz (89 ml) paper cup filled with foam. Once the desired density is reached, whipping is stopped.

Foam Preparation/Drying

Froth prepared as described above is spread on release paper supported by a stiffer web sheet and is smoothed to a height of about 0.25 in (~6.4 mm) or as desired. The froth is placed in a Blue M forced air oven at drying temperature of approximately 60 to 74 deg C. (~140 to 165 deg F.) for about 65 minutes. The dry foam sheet is recovered and slit lengthwise along the axis that parallels the two major surfaces to yield two mirror image sheets of foam having small cell sizes ranging from about 30 to 100 microns on their outer surfaces and larger cell size ranging from about 250 to 800 microns on their inner major surfaces.

EXAMPLE 2

In the manner described in Example 1 above, dispersions, froths and foam samples are prepared. The types and characteristics of the Polymer are described in Table 1 above. The froth stabilizer, any additive and surfactants, the composition of the dispersions and the properties of the Foams are described in the following Tables 2 and 3. The Polymer is selected from a broad series of ENGAGE elastomer (ethylene/1-octene copolymer resin), a product available from DuPont Dow Elastomers, or an analogous copolymer from the same source with 1-butene substituted for 1-octene. Unicid 350 dispersant is a 26 carbon (average chain length) fatty acid. Unicid 425 dispersant is a 32 carbon (average chain length) fatty acid. The fatty acids are utilized in their potassium salt as formed in the extrusion step described above. Frothing surfactant Stanfax 318 surfactant is sodium sulfosuccinimate and Steol CS-130 is a sodium long chain alkyl ether sulfate. The last two surfactants, when utilized, are added with dilution water near point of exit of the melt from extruder in the extrusion step described above.

TABLE 2

Polymer Dispersion Characteristics

| Dispersion Designation | Dispersant (wt % based) (on total solids) | Polymer & Content (wt % solids) | Particle Size (microns) | Polymer Melting Temp. Range (deg C.) |
|---|---|---|---|---|
| 2.1 | 6% Unicid 425 | 1A 60.2% | 1.56 | 25-60 |
| 2.2 | 6% Unicid 425 | 1E 54.5% | 1.69 | 30-90 |
| 2.3 | 6% Unicid 425 | 1J 53.9% | 1.18 | 65-110 |
| 2.4 | 6% Unicid 350 | 1B 59.0% | 0.55 | 25-70 |
| 2.5 | 6% Unicid 350 | 1C 57.2% | 0.72 | 25-80 |
| 2.6 | 2% Unicid 350 | 1C 54.8% | 1.02 | " |
| 2.7 | 6% Unicid 350 | 1F 55.0% | 0.69 | 30-100 |
| 2.8 | 6% Unicid 350 | 1G 55.6% | 0.71 | 25-100 |
| 2.9 | 6% Unicid 350 | 1H 50.6% | 0.70 | 50-110 |
| 2.10 | 6% Unicid 350 | 1D 50.9% | 0.84 | 30-80 |
| 2.11 | 2% Unicid 350 | 1D 53.0% | 0.95 | " |
| 2.12 | 3% erucic acid | 1D 48.4% | 0.85 | " |
| 2.13 | 3% oleic acid | 1D 55.6% | 2.23 | " |
| 2.14 | 2% Unicid 350 + 2% Stanfax 318 | 1D 55.2% | 1.17 | " |
| 2.15 | 2% Unicid 350 + 4% Stanfax 318 | 1D 54.1% | 1.05 | " |
| 2.16 | 2% Unicid 350 + 2% oleic acid | 1D 58.2% | 1.56 | " |

TABLE 2-continued

Polymer Dispersion Characteristics

| Dispersion Designation | Dispersant (wt % based) (on total solids) | Polymer & Content (wt % solids) | Particle Size (microns) | Polymer Melting Temp. Range (deg C.) |
|---|---|---|---|---|
| 2.17 | 2% Unicid 350 + 2% Steol CS 130 | 1D 51.8% | 1.06 | " |
| 2.18 | 4% Unicid 350 | 1K 50.1% | 0.75 | 25-75 |

In Dispersions 2.14, 2.15 and 2.17, the Stanfax and Steol products are added to perform as the Frothing Surfactant in a following frothing step.

EXAMPLE 3

Froth and Foam Preparation

Samples 3A, B, C and D of dispersions are prepared in similar fashion as those designated above in Table 2 as Dispersion 2.10 and Dispersion 2.12 from Polymer 1D. Sample 3A uses 6% Unicid 350 dispersant, while Samples 3B, C and D each use 3% erucic acid as dispersant in preparation of the base dispersion. Each of the dispersion Samples 3A-D is frothed with 1% Steol CS-130 surfactant, together with 0.2% active weight of Methocel E4M hydroxypropyl methylcellulose in the manner described earlier. The froths of the ethylene/1-octene copolymers are dried at approximately 167 deg F. (75 deg C.), and that of the ethylene/1-butene copolymer at approximately 140 deg F. (60 deg C.), in a forced air oven. Sample 3D is dried in a slightly different fashion, being placed in an infrared heated "oven" and passed through quickly first, before being placed in the standard forced air oven to complete the drying process. This serves to more quickly dry the foam surface than the other technique. When examined using SEM, the open cell foams from dispersions 3A through D exhibit cell size gradient from small cells on the outer surface to larger cells in the interior of a foam sheet sample. The character of the foam cell size for all foams is relatively similar, having about 70% to 80% of the cells of size less than 50 microns, about 10-15% of cell size between 50 and 100 microns and about 10% greater than 100 microns cell size. Foam density for the 4 foam samples vary from 73 g/L for Sample 3A, 97 g/L for Sample 3B, 44 g/L for Sample 3C and 56 g/L for Sample 3D.

EXAMPLE 4

Additional Foam Preparations & Testing

In the fashion of Example 3, several different dispersions are prepared, frothed and dried to durable foam. Formulations of the dispersion and froth blends are shown below in Table 3.

Wicking Height Testing

Vertical wicking testing of foams prepared as described above is conducted for 5 minutes in die fashion described earlier with 0.9% saline solution. The results suggest that highly hydrophobic dispersants such as the Unicid dispersants render a resulting foam relatively hydrophobic and therefore do not wick aqueous fluid well, but are useful for absorbing hydrophobic fluids (oil spill clean-up, etc.). Aqueous wicking typically improves when less of a hydrophobic dispersant is used.

TABLE 3

Polymer Foam Characteristics
(active component percentages, based on Polymer weight)

| Dispersion Designation | Polymer | Dispersant & amount | Frothing Surfactant | Methocel E4M amt. | Wicking Ht. (cm) |
|---|---|---|---|---|---|
| 3.1 | 1A | Unicid 425 6% | Stanfax 318 1.7% | 0.4% | 0 |
| 3.2 | 1B | Unicid 350 6% | Steol CS-130 2% | 0.1% | 1.4 |
| 3.3 | 1C | Unicid 350 2% | Na Lauryl sulfate 1.5% | 0.3% | 1.0 |
| 3.4 | 1E | Unicid 425 6% | Steol CS-130 1% | 0.2% | 0 |
| 3.5 | 1J | Unicid 350 6% | Stanfax 318 3.3% | - none - | 0.5 |
| 3.6 | 1D | Unicid 350 6% | Steol CS-130 1% | 0.2% | 0 |
| 3.7 | 1D | Erucic acid 3% | Steol CS-130 1% | 0.2% | 3.0 |
| 3.8 | 1D | Erucic acid 3% | Stanfax 318 1% | 0.3% | 1.5 |
| 3.9 | 1D | Oleic acid 6% | - none - (Oleic acid serves dual purpose) | 0.2% | 2.1 |
| 3.10 | 1D | Oleic acid 3% | - none - (Oleic acid) | 0.2% | — |
| 3.11 | 1K | Unicid 350 4% | Oleic acid 0.4% | 0.4% | 0.2 |

EXAMPLE 5

Filler Additive

A sample of foam is prepared in the manner described for Foam 3.7 in Example 4, above, except that about 14% of a cotton fiber (of about 0.15-0.25 in, average fiber length) is added to the blending step before the dispersion is frothed and dried to prepare the Foam of the invention. The resultant Foam is very uniform, has excellent flexibility and softness and exhibits good absorbency and improved rewetting capabilities and a less elastic character and higher tensile strength, than the same Foam without the cotton fiber additive.

EXAMPLE 6

Foam Laminate Structure

A sample of Froth is prepared in the manner described for Foam 3.7 in Example 4, above, except that the prepared Froth is doctored onto a sheet about 2 mm thick and 75 mm wide of an open-cell (over 80 volume percent open) extruded polyolefin foam. The Froth is then dried on that sheet in a forced air oven at 75 deg C. for 30 minutes. The extruded polyolefin foam is prepared by extrusion of a thermoplastic melt through a multi-orifice die, using apparatus and techniques described in U.S. Pat. Nos. 3,573,152 and 4,824,720 (each of which is incorporated here by reference). The blend of polyolefin resins in the thermoplastic melt has a medium flexural modulus (about 110 kpsi by ASTM D790), and to the melt is added suitable amounts of nucleating agent, blowing agent and other optional additives if desired. Based on weight of the melt, as a nucleating agent about 0.5% talc is employed, and about 3.5% iso-butane and 4% carbon dioxide are employed as blowing agents, to prepare the extruded polyolefin foam sheet.

The surface of the recovered extruded profile is skived to remove a thin skin or closed cells on the surface and to expose an open-cell surface of average cell size about 580 microns (as determined according to ASTM D2856-A). Then a thin foam layer is sliced from that skived surface to yield a foam sheet of desired predetermined thickness of about 2 mm. The drying step noted above causes good bonding of the Froth-derived Foam to the extruded foam's skived surface at the drying temperature to be employed.

EXAMPLE 7

Post Driving Foam Cell Structure Re-Orientation

In the manner described previously in Example 3, a sample of foam is prepared from a frothed dispersion of AFFINITY EG 8200 resin, an ethylene/1-octene, 62%/38% copolymer of melting range approximately 30-80 deg C., a density of 0.870 g/cc and 5 g/cc melt index (ASTM D 1238@190 deg C./2.16 kg) available from The Dow Chemical Company. A dispersion of same having about 55 wt % (dry) polymer solids and average particle size of about 1 micron, prepared using 2% Unicid 350 dispersant and 2% Hystrene 4516 frothing surfactant (a high purity, fatty acids mixture, typically comprising about 55% stearic, 42% palmitic and 0.5 to 1.5% each of margaric, myristic and pentadecanoic acids available from Humko Chemical Div. of Witco Corp., Memphis, Tenn., and subsequently neutralized with potassium hydroxide to form the acid salts) is frothed, doctored on a conveyer belt and thereafter dried to give a foam of density about 0.025 g/cc. Drying is carried out continuously by conveying the froth through a Blue M forced air oven at temperature of about 75 deg C. Total time in the drying environment is about 7 to 9 minutes, on average. The resulting foam sheet layer is fed, at speeds of between 5 and 25 feet/min (about 150 to 750 cm/min) through the nip of two rollers. One roller (rubber coated) is unheated and contacts a Major Surface of the foam at a temperature of 22 deg C., while the second roller (steel) is heated to contact the opposite Major Surface at varying temperatures between about 22 and 55 deg C. (~72 to 131 deg F.). Pressure applied to the foam sheet layer by the rollers, in a substantially uniform fashion across each Major Surface, is varied between about 10 psig to about 80 psig (about 70 kPa to about 550 kPa, gauge pressure). The original sheet thickness ranges from about 3.42 to about 3.78 mm. After the sheet is heated, compressed and cooled, samples are measured for their reduction in thickness between the two Major Surfaces. Then duplicate strips are cut from each sample and subjected to the VWH test as previously discussed. The heat and pressure conditions and the properties of the processed foam samples are recorded in Table 4, found below. A "+" sign indicates that VWH exceeds the length of the sample strips. Foam from Froth made as described, using the long chain fatty acid salts (e.g., Hystrene 4516) has a fabric-like "hand", that is a soft, fabric-like surface is imparted to the finished Foam, in contrast to Foams made from Froth not containing such fatty acids.

TABLE 4

Foam Treatment Conditions and Resultant VWH Characteristics

| Sample * | Roller Speed (ft/min)/ (m/min) | Roller Pressure (psig/ kPag) | Roller Temp (° C.) | Original Foam Thickness (mm) | Thickness Compression + 5 minutes - (mm) | % of Orig. Thick (%) | Compression + 24 hours (mm) | Compression + 48 hours - (mm) | % of Orig. Thick (%) | Vertical Wicking Ht. (VWH) (cm) |
|---|---|---|---|---|---|---|---|---|---|---|
| 1, 2 | 5/1.5 | 10/69 | 22 | 3.64 | 3.22 | 88 | 3.32 | 3.30 | 91 | 1.6 |
| 3, 4 | 5/1.5 | 30/207 | 22 | 3.78 | 3.41 | 90 | 3.55 | 3.57 | 95 | 1.65 |
| 5, 6 | 5/1.5 | 80/552 | 22 | 3.61 | 3.36 | 93 | 3.48 | 3.48 | 97 | 1.55 |
| 7, 8 | 5/1.5 | 80/552 | 38 | 3.49 | 2.99 | 85 | 3.29 | 3.19 | 91 | 2.25 |
| 9, 10 | 5/1.5 | 80/552 | 47 | 3.42 | 2.25 | 66 | 2.43 | 2.46 | 72 | 9.1+ |
| 11, 12 | 5/1.5 | 80/552 | 50 | 3.57 | 2.04 | 57 | 2.06 | 2.05 | 57 | 9.1+ |
| 13, 14 | 5/1.5 | 80/552 | 55 | 3.61 | 0.86 | 24 | 0.88 | 0.88 | 24 | 10+ |
| 15, 16 | 10/3.1 | 80/552 | 55 | 3.51 | 1.90 | 54 | 1.92 | 1.90 | 54 | 8.5 |
| 17, 18 | 18/5.5 | 80/552 | 55 | 3.72 | 2.42 | 65 | 2.49 | 2.55 | 68 | 10+ |
| 19, 20 | Control | No compression | — | 3.64 | — | — | — | — | — | 1.15 |

* Data from average of two samples.

The invention claimed is:

1. A stable, aqueous froth consisting essentially of the reaction product of: a) one or more copolymers or interpolymers of ethylene and/or 1-propene with or without other monomers selected from $C_4$ to $C_{10}$ olefins and having an ethylene or 1-propene content from about 2-98 weight percent;
b) water; c) a frothing surfactant; and d) a gas; where the components comprise about: a) 35 to 75 percent, b) 35 to 75 percent and c) 1 to 6 percent of the combined weight of a), b) and c), and d) is present in an amount such that d) comprises at least 80 percent of the total volume of all components present in the froth.

2. The froth of claim 1 which further comprises component e) a foam stabilizer selected from: alkylcellulose ethers, hydroxyalkyl cellulose ethers, hydroxyalkyl alkylcellulose ethers, guar gum, xanthan gum, and polyoxyethylene resins of at least 20,000 molecular weight, said component e) present in the amount of from about 0.05 to about 2 percent based on the dry weight of component a) polymer.

3. The froth of claim 1 where component a) is a copolymer of ethylene with an alpha-olefin comonomer of from 3 to 10 carbon atoms.

4. The froth of claim 3 where the alpha-olefin comonomer is selected from 1-propene, 1-butene, 1-hexene and 1-octene and component a) has a melt index between about 0.5 and about 30 g/10 mm as determined by ASTM D1238 (condition 190 deg C./2.16 kg).

5. An absorbent article selected from a baby diaper, a feminine hygiene product, an adult incontinence hygiene product, a wound dressing pad, a surgical sponge, a food packaging pad, a wiping towel and a wiping sponge, where the article comprises a component made from any one of the froths of claims 1, 2, 3, and 4.

6. A laminate comprising at least one layer of the froth of any one of claims 1-4, and at least one substrate layer on which the said froth layer is laid, doctored or spread.

7. A laminate of claim 6 wherein the at least one substrate layer is prepared from a layer of a second froth, a preformed open-cell foam, a thermoplastic sheet or film, a woven or non-woven fabric, or melt spun-bonded or melt-blown material.

8. A laminated structure of claim 6 wherein the at least one substrate layer is selected from a layer of a second open-cell foam, a thermoplastic sheet or film, a woven or non-woven fabric, or melt spun-bonded or melt-blown material.

9. An absorbent article selected from a baby diaper, a feminine hygiene product, an adult incontinence hygiene product, a wound dressing pad, a surgical sponge, a medical garment, a surgical drapery, a wiping towel, a wiping sponge and a food packaging pad, wherein the article comprises a component made from the laminated structure of claim 8.

* * * * *